(12) United States Patent
Lüscher (10) Patent No.: US 6,440,098 B1
(45) Date of Patent: Aug. 27, 2002

(54) DEVICE FOR IMPLANTING FILAMENTOUS MATERIALS

(76) Inventor: Patrik Lüscher, Steinwiesstrasse 7, CH-8330 Pfäffikon (CH)

( * ) Notice: Subject to any disclaimer, the term of this patent is extended or adjusted under 35 U.S.C. 154(b) by 0 days.

(21) Appl. No.: 09/508,709

(22) PCT Filed: Sep. 14, 1998

(86) PCT No.: PCT/CH98/00393

§ 371 (c)(1),
(2), (4) Date: Apr. 12, 2000

(87) PCT Pub. No.: WO99/13781

PCT Pub. Date: Mar. 25, 1999

(30) Foreign Application Priority Data

Sep. 16, 1997 (CH) .............................................. 2188/97

(51) Int. Cl.[7] .............................................. A61M 31/00
(52) U.S. Cl. .............................. 604/57; 604/13; 604/15; 604/60; 604/288.03
(58) Field of Search ................................ 604/11, 13, 15, 604/19, 57, 59, 60, 167.02–167.04, 167.06, 202, 213, 237, 249, 256, 264, 236, 288.03, 537

(56) References Cited

U.S. PATENT DOCUMENTS 4,994,069 A * 2/1991 Ritchart et al. ............. 604/104
5,167,624 A 12/1992 Butler et al. .................. 604/60
5,499,995 A 3/1996 Teirstein ..................... 606/192
6,299,590 B1 * 10/2001 Luscher et al. .............. 604/11

FOREIGN PATENT DOCUMENTS

| EP | 0734697 | 3/1996 | ............. A61F/2/02 |
| EP | 0769307 | 10/1996 | ............ A61M/15/10 |
| WO | 9426175 | 11/1994 | ............. A61B/17/12 |
| WO | 9604954 | 2/1996 | ............. A61M/37/00 |
| WO | 9719643 | 6/1997 | ............. A61B/17/12 |

* cited by examiner

Primary Examiner—Gregory Huson
Assistant Examiner—Tuan Nguyen
(74) Attorney, Agent, or Firm—Volpe and Koenig P.C.

(57) ABSTRACT

A device for applying a filamentous implant by means of a pressure-generating and fluid-containing unit which is connected to a housing containing the thread to be implanted. The housing opens out into a channel used for delivering the thread externally. The pressure generation unit generates a static pressure on a fluid contained inside the device, said fluid pushing the thread to be implanted through the distal narrowed tip of the channel, towards the exterior or into a tissue or a body cavity. The fluid remains inside the device in the course of this process. The distal end of the device can be plugged in order to prevent the fluid from exiting after application of the implant. The application can be stopped once an adequate quantity of the implant material has been implanted by severing the thread in the vicinity of the distal end of the channel or at the proximal end.

25 Claims, 13 Drawing Sheets

DEVICE FOR IMPLANTING FILAMENTOUS MATERIALS

The invention relates to a device for applying a thread-like implant with a pressure-generating, fluid-containing means that is connected with a casing accommodating the thread to be implanted, wherein the casing empties into a channel. The thread to be applied is introduced into the distal end of the channel. The pressure exerted on the fluid by the pressure-generating means enables transport of the thread to be implanted and located inside the casing through the distal opening of the channel, where the thread is discharged to the outside, or into a tissue or hollowed out body. Since the arrangement discharges the implant in threadlike form and through the channel, there is a potential application for operative microscopy.

Devices for applying a threadlike implant were already disclosed in WO 96 04954. A stream of fluid is generated in this channel, which transports the thread to be implanted through the channel. The fluid is then discharged along with the thread through the distal opening of the channel.

The object of the invention is to provide a device that can be used to apply a ball-shaped implant into a tissue or hollowed-out body, wherein the fluid necessary for transporting the thread remains in the device. The object is achieved according to the characterizing clause of claim 1.

The present invention makes it possible to inject the thread to be implanted against higher resistances. Since more force can be exerted on the thread with the device according to the invention in comparison to the devices in WO 96/04954, less flexible threads can also be implanted. In addition, the device according to the invention enables a minimally invasive implantation of threadlike implant materials without simultaneously discharging a fluid into the body. If threadlike implant materials and a fluid must be implanted together for certain medical applications, this can take place via two separate channels. As opposed to the devices described in prior art, the advantage to this is that implant material and fluid can be metered in separately and independently of each other. Likewise, the implanted thread volume can be precisely controlled and metered, because the volume forced out by the pressure-generating means corresponds to the implanted thread volume.

The implant applied with the device according to the invention is characterized by a thread ball in the form of a three-dimensional, open-pored structure. This thread ball is incorporated at a desired spot into the tissue or another point of the body to be treated via a small puncture or a hole in the body in operative microscopy, and in any amount. The thread ball is formed when the thread to be applied encounters a resistance in the tissue after exiting from the distal end of the channel, so that the ensuing thread sections are bent and finally stacked to form the desired thread ball. By moving the distal channel end while implanting a thread, the form of the implant can be varied within a wide framework and fixed intraoperatively. This yields a wide range of potential applications. The pore size and structural properties of the implant can be varied, for example via the diameter of the thread or by modifying the material properties of the thread, in particular bending strength, and can be set pursuant to the clinical requirements. The thread can be a carrier of biologically active substances, and is particularly suited for the controlled administration of drugs or induction of body tissue.

The device according to the invention is used, for example, during the treatment of urinary incontinence, for which a thread ball is injected into the tissue below the neck of the bladder to lift it. In addition, as described in WO 96/04954, it is used in the treatment of bone defects and plastic surgery in the form of tissue-inducing threads, which induce the generation of new bony, cartilage or connective tissue through the release of growth factors. In addition, the device according to this invention is used for the treatment of fistulas, aneurisms and therapeutic embolisation of blood vessels. Another important application is use as a "drug delivery system", for example through the local administration of cytostatics for cancer treatment, or the release of antibiotics for the treatment of infections. Another example involves cell transplantation, in which the threads are implanted with incorporated cells, e.g., Langerhan's cells, using the device according to the invention.

The examples of the device according to the invention enumerated here constitute only a limited selection of various applications.

The device according to the invention is characterized by an opening in the area of the distal end of the mentioned channel. In terms of diameter or cross-sectional surface, this opening essentially corresponds to the threadlike implant material, which can also be a thread with non-circular cross section. The threadlike implant material is shifted through the opening via a pressure difference, during which no fluid stream is moved, as opposed to the design known from WO 96 04954. The fluid is only used to hydraulically convey the hydrostatic pressure built up by the pressure-generating means to the thread, which as a result gets pressed out of the distal opening of the channel of the device. As opposed to devices known from prior art, the device according to the invention does not envisage any fluid exiting from the opening along with the thread.

A non-compressible substance, e.g., water or oil, is suitable as a fluid to be used according to this invention, since the discharge of the thread into the tissue can be better monitored. For example, if the necessary pressure is applied via a piston pump-like system, a high pressure can be applied with vary little piston travel in the case of incompressible fluids, and the amount of implanted material corresponds to the displaced volume in the piston. In addition, the advantage to incompressible fluids is that the pressure can be diminished very rapidly and without fluid expansion.

Suitable incompressible fluids according to the invention include water, aqueous solutions (e.g., saline solutions), oils such as Soya bean oil, castor oil or paraffin, liquids with various additives, which help the thread slide through the opening in the device according to the invention, while compressible media include gases, such as nitrogen.

Another advantage to the invention lies in the fact that, in addition to threads with a high bending strength, use can also be made of very readily soft and flexible threads, e.g., rubbery threads, which more readily result in the desired irregular, spongy ball structures that are better suited for most applications in medicine than regular structures. However, regular structures can be an advantage for various applications.

Threadlike implant materials can include structures that exhibit a long length in comparison to the diameter, and which have a bending strength low enough that they can be shaped into ball-like structures during implantation. These structures can exhibit circular or differently shaped cross sections, or be monofilaments or multifilaments. It is important that the threadlike materials seal the distal narrowing of the channel in such a way that essentially no fluid can get out of the device. The distal narrowing can be shaped to reflect the thread cross sections, first to ensure a good seal, and second to simultaneously achieve passage of the thread through the narrowing with as little friction as possible.

In special cases, it is also conceivable to use threads with a higher bending strength, which cannot form any ball structures inside the body, e.g., to linearly advance a thread in the tissue using the device according to the invention, or to apply ordered structures, e.g., in the form of flat spiral springs.

Suitable materials for the threadlike implant include. synthetic polymers, such as silicone elastomers, polyhydroxymethacrylate (PHEMA) and hydrogels consisting of PHEMA, polyurethane, Dacron, polyesters such as polylactides or polyglycolides and polyorthoesters. Suitable bipolymers include collagen, gelatins, hyaluronic acid, chitosane and alginate. In addition, use can be made of composite materials such as monofilaments with reinforced threads comprised of glass threads, polymer threads or ceramic threads, as well as monofilaments mechanically reinforced by one or more long threads or a multifilament, monofilaments with incorporated particles, monofilaments comprised of various materials (resorbable or non-resorbable), e.g. with laminated structure, porous monofilaments, monofilaments that swell inside the body (quellable PHEMA or other hydrogels), monofilaments with X-ray contrast (also via incorporation of particles or threads or threads with X-ray contrast).

Injecting threads via the procedures known from prior art can under certain conditions be difficult if space for the implant in the tissue must be created during injection, e.g., as is the case in so-called"tissue bulking". The force that must be exerted on the threads in this case to deposit them into the surrounding tissue is relatively high. According to the procedure described in WO 96/04954, the thread often becomes blocked during the implantation process, since a relatively low force is applied to advance the thread against the resistance of the tissue in the channel. The thread is advanced via the fluid used in WO 96/04954, which can be introduced with a corresponding pressure. The force on the thread can only cause the hollow space created by the fluid to be filled out by the thread material. Therefore, the structure of the implant will be very loose, and only contract or compact as the fluid is resorbed or siphoned off. The implant must be a specific size in the aforementioned "tissue bulking". Often, space for the implant cannot be created by overstretching, so that the desired volume can be reached later. In addition, it would likely be very difficult to meter the necessary thread amount, i.e., the implant volume, under these conditions.

Therefore, another advantage to the present procedure lies in the fact that the thread can be pressed directly into the tissue, and at most only a slight reduction in implant volume can be expected from changing the ball structure. In addition, it is possible to use soft threads with a higher bending strength in comparison to WO 96/04954, which cannot be applied with the device described in WO 96/04954.

Depending on clinical application, it may make sense to apply one or more threads with predetermined length, or to terminate application after a sufficient amount of threadlike implant material has been implanted. In the former case, the sudden exit of pressurized fluid after ejection of the proximal thread end is prevented by sealing the distal opening, or using a check valve between the pressure-generating means and casing. In the latter case, the thread is cut near the distal end of the channel or more proximally after the application of enough implant material. The distal part of the cut thread can then be completely ejected from the device before the channel is retracted from the treated body.

Additional features and advantages of this invention arise from the subclaims, the description and the figures. Embodiments of the invention will be described below based upon the figures. Shown on:

Figure 1:
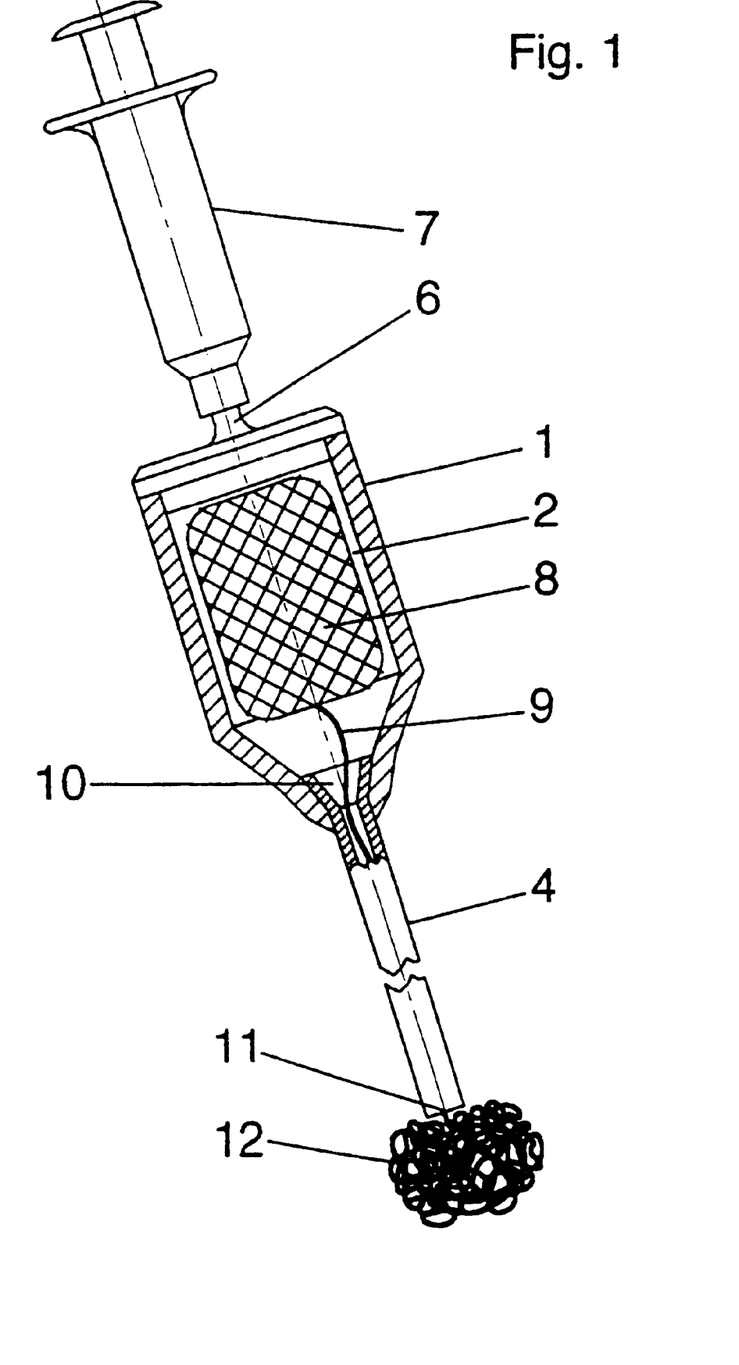
FIG. 1 is a diagrammatic view of a device according to the invention.

In FIG. 1, the device according to the invention exhibits a casing 1, which has an interior space 2, which empties into a channel 4, and is connected, for example, with a syringe-like pumping device 7 via an additional channel 6. The interior space of the device (2, 7, 4) is filled with a fluid.

In another embodiment not shown here, the pumping device 7 can also be directly connected to the channel 4, bypassing the casing 1.

Located within the interior space 2 is a thread wound into a bobbin 8, which can be pulled off of the bobbin from the inside over the head. In another embodiment of this invention, the thread 9 can also be wound into a spool and accommodated inside casing 1 on a rotatable axis or in the form of other dispensing tools not shown here. A thread 9 wound onto the spool or bobbin is retracted through a proximal opening 10 of the channel 4, the channel 4 and the distal opening 11 of the channel 4. The channel is designed in such a way that the thread 9 can essentially slide into it without rubbing. In the area of the distal opening 11, the channel 4 is narrowed in such a way that the thread 9 can be passed through the opening 11 and discharged outside, but the fluid is simultaneously retained in the device. The thread 9 is pushed toward the outside through the distal opening 11 by a hydrostatic pressure inside the device generated by the pumping device 7. Depending on the pressure level in the fluid, the transport rate of the thread 9 can be increased or decreased. In this way, it is possible to pass a specific thread length through the distal, narrowed opening 11 while unwinding a bobbin and discharge it to the outside without fluid simultaneously exiting from the device.

The channel 4 is designed in such a way that its distal opening 11 can be advanced through a puncture hole or body opening into the tissue of the part of the body to be treated, or into a hollow space of the body. The channel can be designed as a flexible catheter, rigid or flexible endoscope channel, as an insert into the endoscope channel or trocar, or as a hollow needle. The distal thread end exiting at the opening 11 encounters a resistance in the tissue, so that the ensuing thread sections are bent, and finally stacked to form a thread ball 12, as shown on FIG. 1. This is typically important for the device described in WO 96/04954.

Figure 2A:
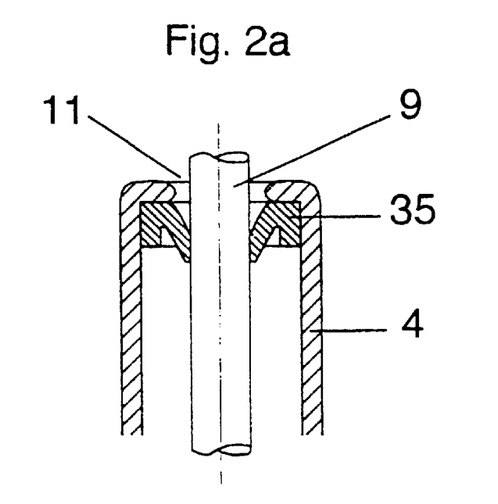
FIG. 2a is a lip seal.

An essential feature of this invention is that basically only the thread 9 exits the distal opening, and the fluid is retained by means of specially designed distal openings. These special designs will be described in the following:

FIG. 2a shows a lip seal 35, which seals the channel 4 at the distal opening 11.

Figure 2B:
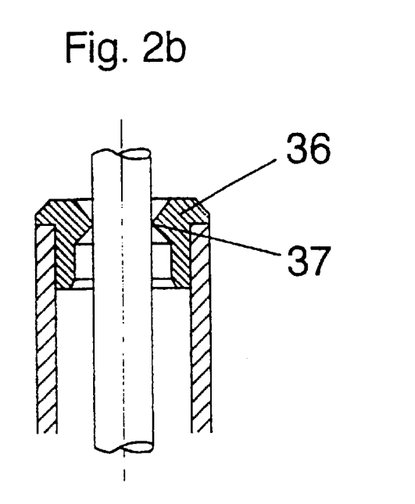
FIG. 2b is a seal insert.

FIG. 2b shows an insert 36 that seals the channel 4 via the edge 37, and is mounted via interference fit, welding and bonding. It serves as a cover both for metal channels as well as hard and soft polymer channels.

Figure 2C:
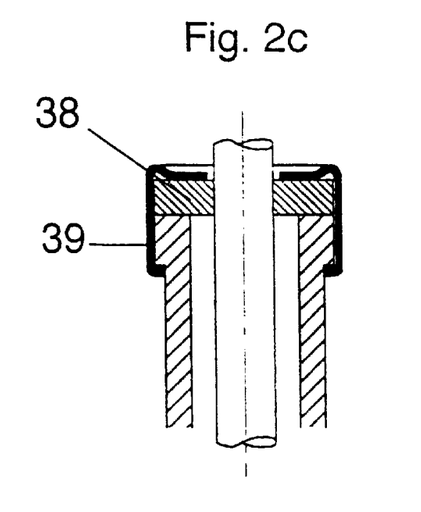
FIG. 2c is a perforated disk seal.

FIG. 2c shows a seal created by means of a perforated disk 38. The perforated disk 38 can consist of hard or soft materials, e.g., rubber. In the embodiment shown here, the disk 38 is affixed with a metal cap 39, wherein the perforated disk 38 is mounted under elastic deformation of the cap 39.

Figure 2D:
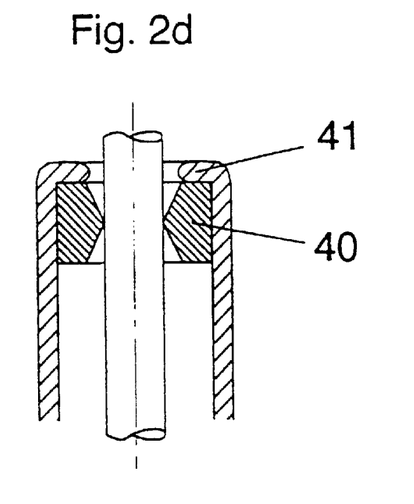
FIG. 2d is a seal insert and bent channel ends.

FIG. 2d shows a sealing insert 40 made out of a hard or soft material, which is fixed using the bent edges 41 of the channel. Another way to fix the sealing insert 40 is to narrow the channel.

Figure 2E:
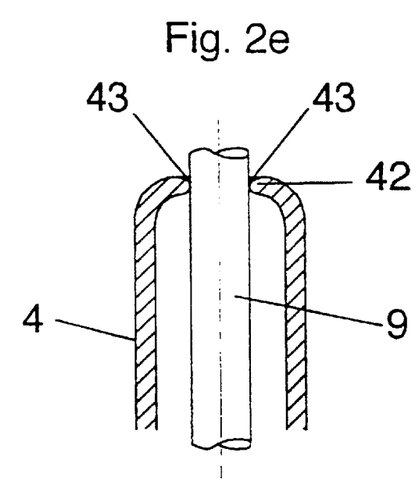
FIG. 2e is a seal created by a narrowing at the channel end.

FIG. 2e shows a narrowing 42 at the end of a metal channel 4, whose edge 43 is shaped with special tools, as shown, wherein the edge 43 can also be rounded to reduce the sliding friction of the thread 9 as it is advanced through the narrowing 42.

Figure 2F:
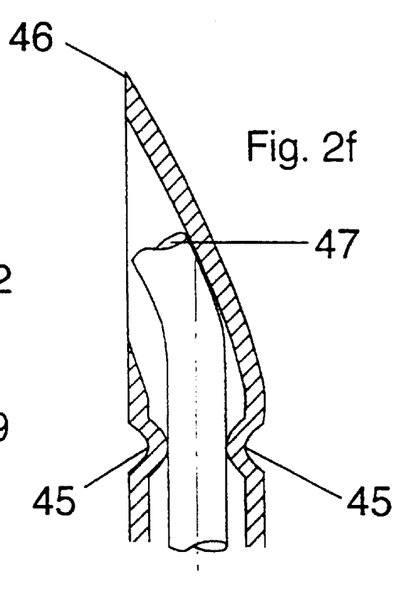
FIG. 2f is a seal created by a narrowing of the channel with beveled channel tip.

FIG. 2f illustrates a channel embodiment in which the seal is brought about by a narrowing 45 of the channel 4. The channel is designed with a bent and ground tip 46 to make it easier to advance the thread into the tissue. The advantage to this embodiment is that the distal thread end 47 is protected as it advances, and cannot be pushed back through the narrowing 45 by the tissue. In another embodiment of FIG. 2f not shown here, the tip can also be straight.

Figure 2G:
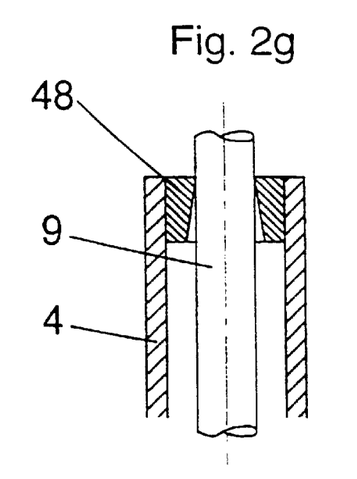
FIG. 2g is a conical seal insert.

FIG. 2g illustrates a conical sealing insert 48 that is fixed via bonding, welding or interference fit. In another embodiment, the cone is not oriented toward the inside as shown, but toward the outside.

Figure 2H:
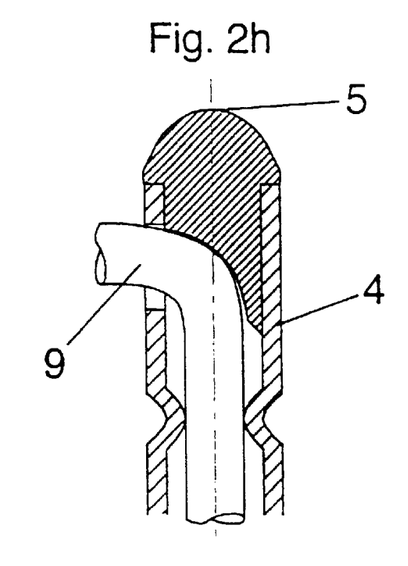
FIG. 2h is a lateral outlet for the thread.

FIG. 2h shows a variant in which the thread 9 is laterally discharged from the channel 4. In another embodiment, the thread outlet can also be further removed from the distal end 5 of the channel 4.

Figure 2I:
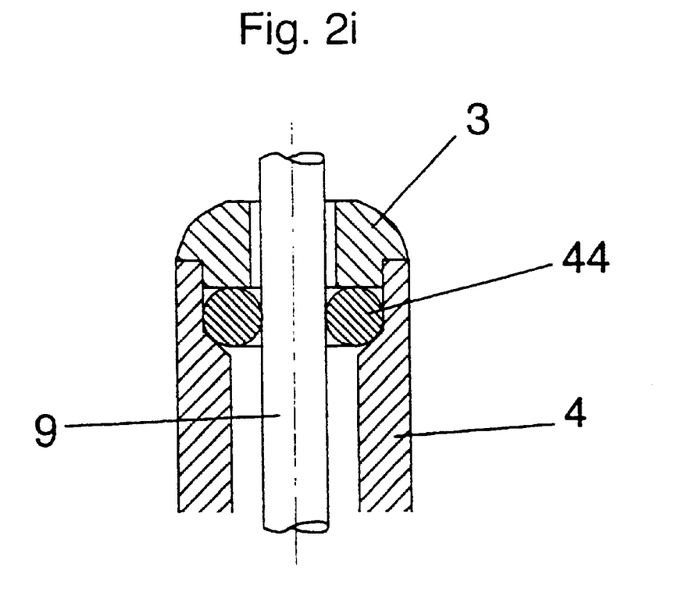
FIG. 2i is an O-ring seal.

FIG. 2i shows an embodiment in which the channel 4 is sealed with an O-ring. In the embodiment shown, the O-ring 44 is fixed with an insert 3, which is mounted via bonding, welding or interference fit.

Figure 3A:
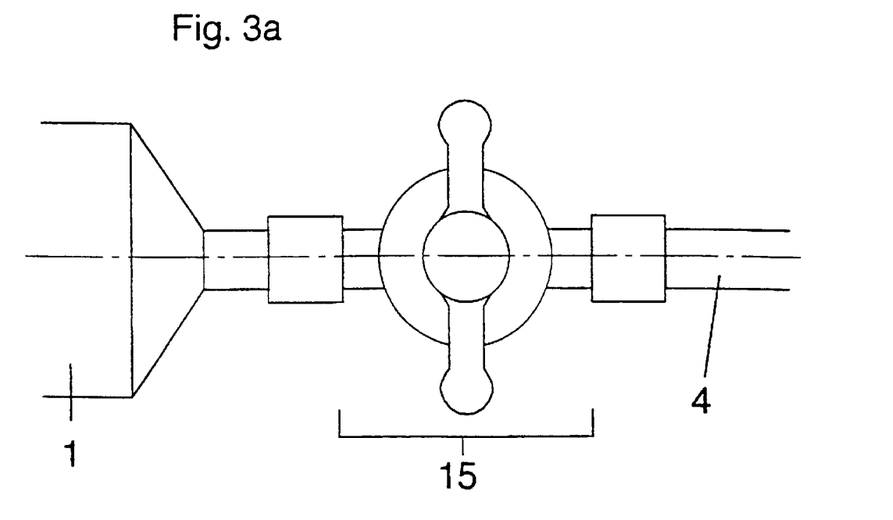
FIG. 3a is a shearing device near the thread storing device.

As another embodiment of this invention, FIG. 3a shows a shearing device 15 for the thread 9 proximal to the distal opening 11 of the channel, which can be manually operated. The shearing device 15 is identical or comparable to conventional valves, e.g., a three-way cock. FIGS. 3a.i and 3a.ii show a diagrammatic section through various embodiments of the shearing device 15. In FIG. 3a.i, the thread proceeding into a borehole 17 is sheared off by a rotation of the cylinder 16 by 90° at the cylinder casing. Due to the second borehole S1, this leaves an open channel for applying the distal part of the thread.

FIG. 3a.ii shows a shearing at sharp edges 13 and 14. The thread 9 runs into the conical borehole 52 in the cylinder 16. Shearing takes place by turning the cylinder 16 by approx. 45°. In the embodiment shown on 3a.ii, a passable channel remains behind after the cylinder is turned back to enable the application of the distal part of the thread 9 remaining in the channel 4. Depending on the material properties of the thread 9, shearing advantageously takes place on blunt or sharp edges.

Figure 3B:
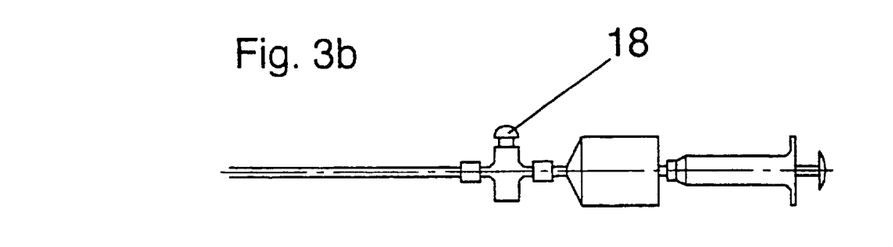
FIG. 3b is a variant with bolt and open throughput.

FIG. 3b shows another embodiment of the shearing device, in which a bolt 18 with two transverse boreholes, one of which (19) guides the thread before and during the application, is pressed laterally into the channel, and shears off the thread 9 when pressed in. A passable channel remains after shearing in shearing device as well due to the second transverse borehole.

Figure 3C:
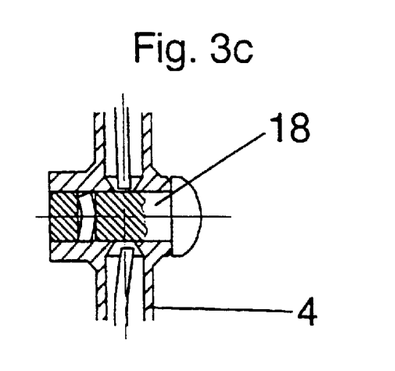
FIG. 3c is a variant with bolt, no open throughput.

FIG. 3c shows another embodiment of the shearing device according to FIG. 3b with a bolt 18 having only one borehole. In this embodiment, the channel 4 is sealed after the thread has been sheared off by pressing in the bolt 18. This variant can be used, for example, when the pressure-generating means 7 is introduced directly into the channel 4 distally to the shearing device, bypassing the casing 1.

FIGS. 4a to 4d show different shearing devices at the distal opening 11 of the device according to the invention, i.e., at the end of channel 4.

Figure 4A:
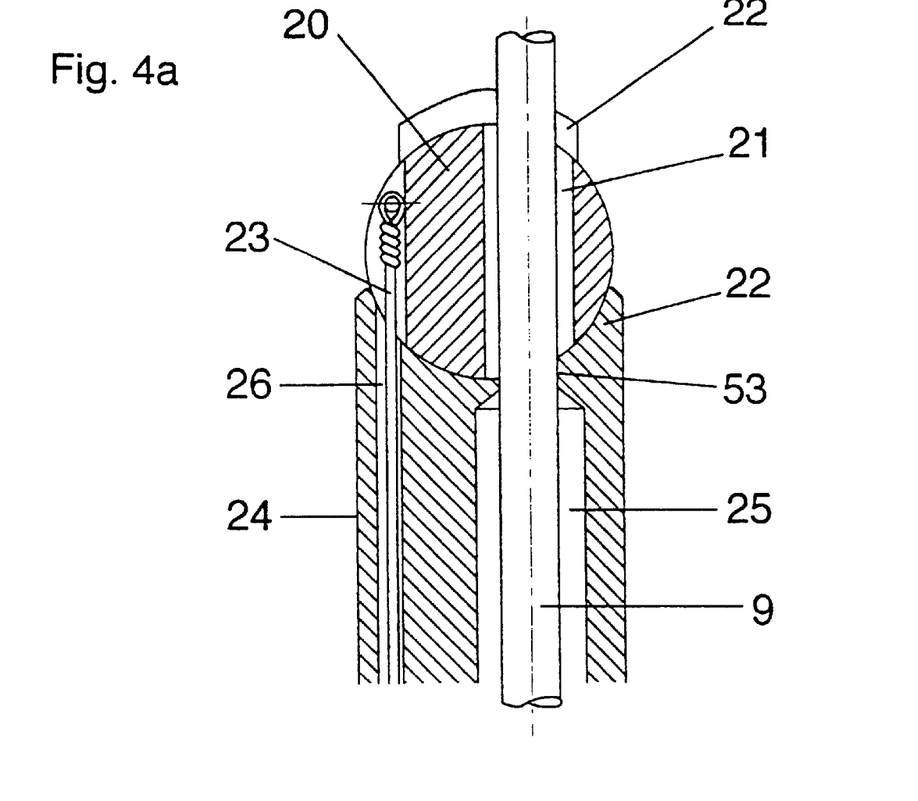
FIG. 4a is a shearing device at the tip of the channel.

FIG. 4a illustrates a system similar to the one described on FIG. 3a. A cylindrical insert 20 with borehole 21 is rotatably snapped into a mount 22. The cylindrical insert 20 can be rotated via a wire pull 23, which shears off the thread 9 and simultaneously seals the lumen 25 (FIGS. 4a.i and 4a.ii). Double-lumen channels 24 are preferably used, wherein the wire pull 23 runs through the lumen 26, and the thread 9 through lumen 25. FIGS. 4a.i and 4a.ii provide a diagrammatic view of the rotational motion of the cylindrical insert 20. This embodiment also has a distal narrowing 53 of the lumen 25 to seal the lumen 25 during the application.

Figure 4B:
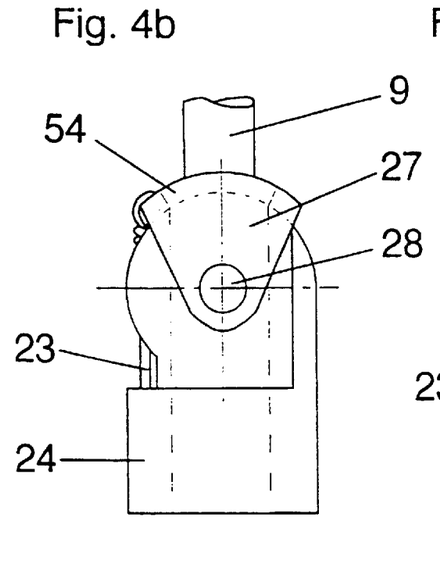
FIG. 4b is a shearing device with bent metal plate with hole.

FIG. 4b shows a system for shearing the thread 9 similar to the one described on FIG. 4a. A bent metal plate 27 pivoted around the axis 28 is located at the distal opening 11 of channel 4, and has a hole 54 at whose edges the thread is sheared off (FIG. 4b.i). The plate is here moved via a wire pull 23. The channel is not sealed in the embodiment shown here.

Figure 4C:
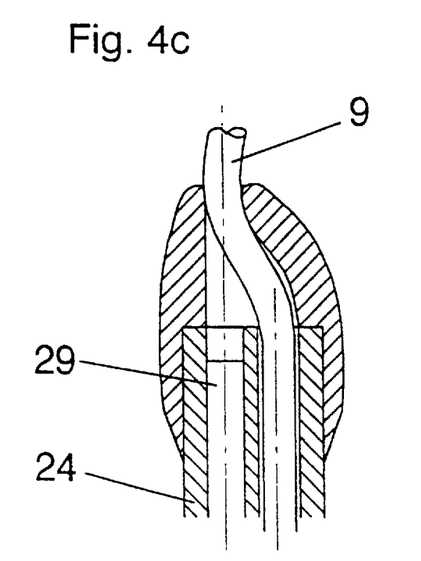
FIG. 4c cutting of thread with a wire.

FIG. 4c shows a shearing device in which the means for shearing the thread 9 is a wire 29. The thread 9 and wire 29 run in separate lumens of the double-lumen channel 24, wherein the volumes converge at the distal end of the channel 24. The tip of the channel is asymmetrically designed to ensure that the wire is guided in a straight line. After the thread has been sheared off, the distal narrowing 30 is sealed by the wire 29.

Figure 4D:
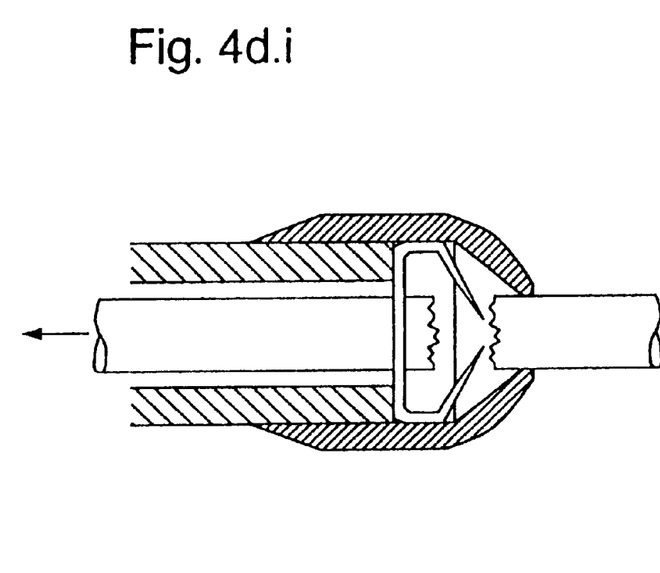
FIG. 4d cutting of thread during retraction from proximal.

FIG. 4d shows a shearing device in which the thread 9 is proximally cut during retraction. In the embodiment shown, this is done by means of a bent plate 55 with sharp edges 56 and 57 and a hole 58, through which the thread 9 is guided during the application. The edges 56 and 57 are in contact with the thread 9. When the thread is proximally retracted (FIG. 4d.i), the edges 56 and 57 cut into the thread 9. The thread 9 is cut through entirely or tears at the weakened location. The thread can be retracted by separating the casing 1 from the channel 4 and pulling on the thread 9 by hand.

Figure 5A:
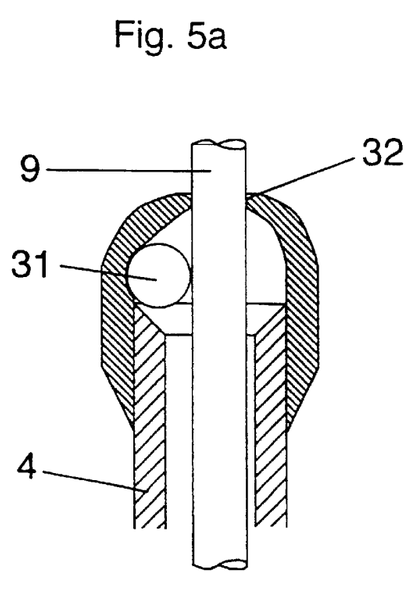
FIG. 5a variant with a ball.
Figure 5B:
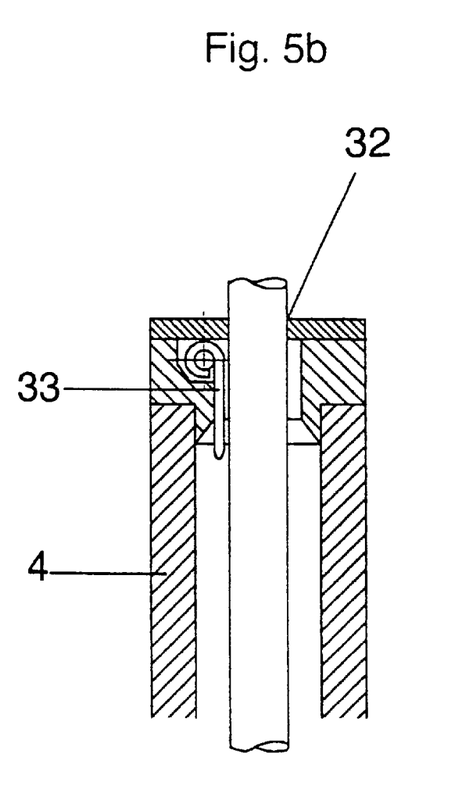
FIG. 5b variant with a pivoted plate.
Figure 5C:
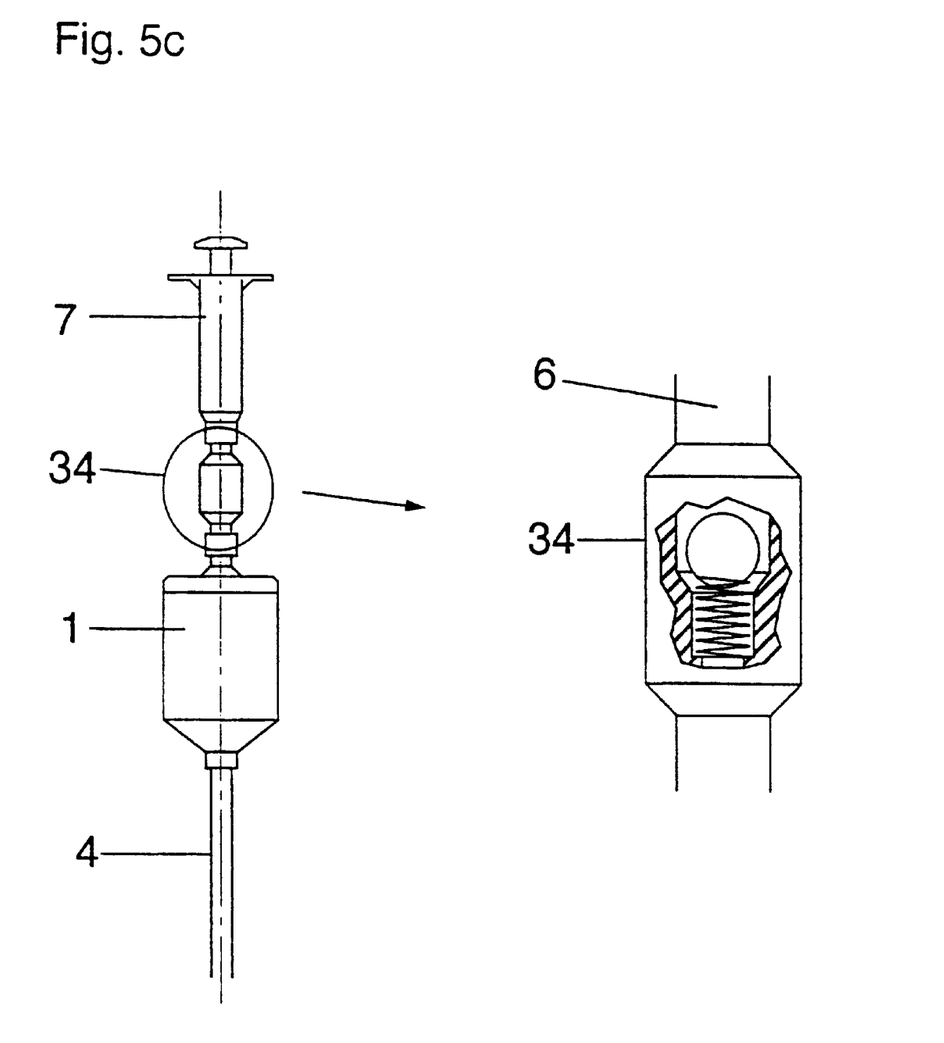
FIG. 5c valve seal.

FIG. 5 shows various sealing devices for the channel 4. Depending on the used fluid and clinical application, it is desirable that very little or no fluid get into the body with the thread 9. After application of a defined thread length, the channel 4 must be closed automatically to prevent the fluid from exiting the distal opening 32 of the channel 4 at an elevated pressure since the latter is no longer sealed by the thread.

FIG. 5a shows an embodiment of a seal for a channel 4 using a ball 31, which is pushed through the fluid to the distal narrowing 32 of the channel after the proximal thread end 49 has exited the channel 4, sealing it as a result.

FIG. 5b shows an embodiment with a pivoted plate 33, which snaps shut and seals the opening of the channel 4 when the proximal thread end 49 has passed the narrowing 32. The force to close the opening can be applied via the fluid, as shown here, or by a spring that can move the plate in another variant not shown here.

FIG. 5c depicts a check valve 34 that is situated between the syringe-like pumping device 7 and the casing 1 enveloping the bobbin 8. Given a sudden higher fluid throughput, as arises when the proximal thread ends exits the distal opening of the channel 4, the valve 34 closes the channel 6 between the pumping device 7 and the casing 1, and thereby stops the injection of fluid.

Figure 6:
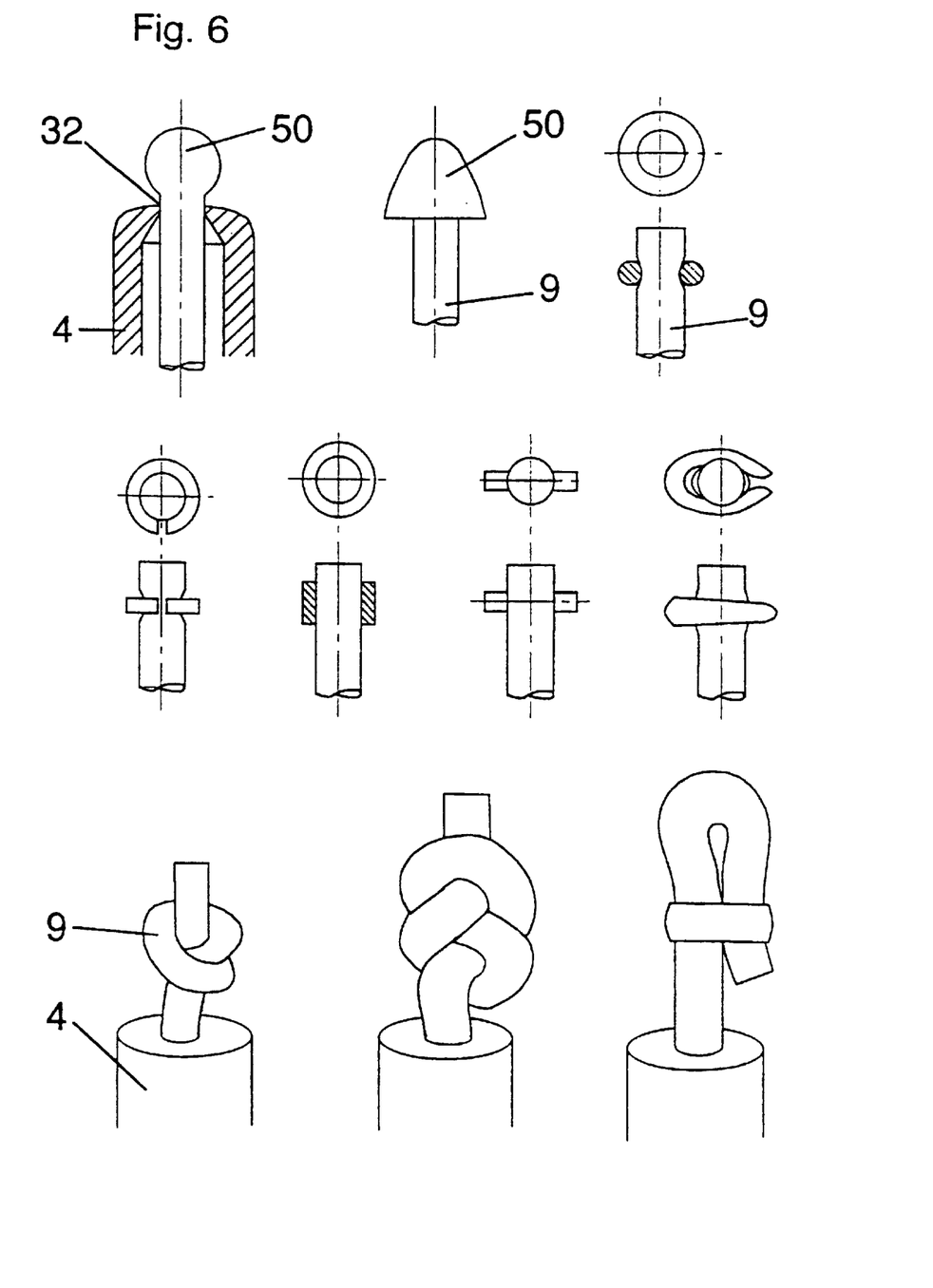
FIG. 6 shaping of distal thread end.

To prevent the distal thread end 50 from slipping through the narrowing 32 at the tip of the channel 4 as the device according to the invention is advanced in the tissue to be treated, thickened areas are introduced at the thread end. FIG. 6 shows various ways of designing the thread end.

What is claimed is:

1. A device for the application of a threadlike implant material, the device comprising: a pressure-generating and fluid-containing means, which is connected to a casing (1) accommodating a thread (9) to be implanted, wherein the casing (1) empties into a channel (4), and the pressure-generating and fluid-containing means transports the thread to be implanted located in the casing (1) out of the device via a fluid in the pressure-generating and fluid-containing means, wherein the pressure-generating and fluid-containing means induces a static pressure on the fluid, and a distal opening (11) of the channel (4) has a means for sealing the fluid within the device and prevents the fluid from exiting the channel.

2. The device according to claim 1, wherein the sealing means is a lip seal (35).

3. The device according to claim 1, wherein the sealing means consists of an insert (36).

4. The device according to claim 3, wherein the insert (36) is applied via interference fit, welding, positive locking or bent edges.

5. The device according to claim 1, wherein the sealing means consists of a perforated disk (38).

6. The device according to claim 1, wherein the sealing means consists of a narrowing at the distal end (11) of the channel (4).

7. The device according to claim 6, wherein the narrowing of the channel is deformed toward the channel interior space.

8. The device according to claim 1, wherein the sealing means is formed by a narrowing of the channel (4) proximal to the distal opening (11) of the channel.

9. The device according to claim 1, wherein the sealing means is a conical insert (48) that narrows toward the outside.

10. The device according to claim 1, wherein the sealing means is an O-ring.

11. The device according to claim 1, wherein the distal opening (11) of the channel (4) is beveled and has a pointed edge (46).

12. The device according to claim 1, wherein a means for cutting the thread is situated proximally to the opening (11) of the channel (4).

13. The device according to claim 12, wherein the means for cutting the thread (9) comprises a cylinder (16) with a borehole (17, 52) guiding the thread, which shears off the thread (9) on the cylinder casing when turned.

14. The device according to claim 12, wherein the means for cutting the thread is a bolt (18), which is laterally inserted into the channel (4).

15. The device according to claim 1, wherein a means for cutting the thread (9) is located at the distal opening (11) of the channel (4).

16. The device according to claim 15, wherein the means for cutting the thread (9) comprises a cylindrical insert (20) with a borehole (21), which can be turned by means of a wire pull (23).

17. The device according to claim 15, wherein the means for cutting the thread (9) comprises a plate (27) with a hole (54), which can be moved my means of a wire pull (23) to shear off the thread.

18. The device according to claim 15, wherein a double-lumen channel (24) is used, wherein a wire pull (23) runs through one lumen (26), and the thread (9) through the other lumen (25).

19. The device according to claim 15, wherein the means for cutting the thread (9) is a wire (29), and that the thread (9) is cut by advancing the wire (29) and by utilizing a distal end (59) of the wire (29).

20. The device according to claim 15, wherein the means for cutting the thread (9) comprises one or more sharp edges for cutting the thread while the thread is being retracted proximally through the channel (4).

21. The device according to claim 15, wherein the means for cutting the thread (9) comprises a bent plate (55), which exhibits two sharp edges that are in contact with the thread.

22. The device according to claim 1, wherein the sealing means is at the distal opening end of the channel (4), which seals the channel (4) after the proximal thread end (49) has exited the latter, while retaining the fluid located in the channel (4).

23. The device according to claim 22, wherein the sealing means is a distal narrowing, which is sealed by means of a ball (31).

24. The device according to claim 22, wherein the sealing means comprises a pivoted plate (33), which snaps in the direction of the distal opening (11) of the channel (4) after the proximal thread end (49) has exited, and seals it.

25. The device according to claim 24, wherein a check valve (34) is inserted after the pressure-generating and fluid-containing means, which closes after the proximal thread end (49) has exited the channel (4) due to a rise in the fluid flow, and thereby prevents fluid from being injected into the body.

* * * * *